United States Patent [19]
Behme

[11] Patent Number: 5,401,744
[45] Date of Patent: Mar. 28, 1995

[54] USEFUL HEMI-HYDRATE FORM OF A CEREBRAL FUNCTION ENHANCING AGENT

[75] Inventor: Robert J. Behme, Newburgh, Ind.

[73] Assignee: Bristol-Myers Squibb Company, New York, N.Y.

[21] Appl. No.: 130,957

[22] Filed: Oct. 4, 1993

[51] Int. Cl.6 .................. C07D 401/14; A61K 31/505
[52] U.S. Cl. ...................................... 514/256; 544/329
[58] Field of Search ................ 544/335, 329; 514/256

[56] References Cited

U.S. PATENT DOCUMENTS

| | | | |
|---|---|---|---|
| 4,826,843 | 5/1989 | Mattson et al. | 544/335 |
| 4,963,678 | 10/1990 | Madding et al. | 544/335 |
| 5,098,904 | 3/1992 | Mattson et al. | 544/335 |

*Primary Examiner*—John M. Ford
*Attorney, Agent, or Firm*—Richard P. Ryan

[57] ABSTRACT

The hemi-hydrate form of the cerebral function enhancing agent 1-[[1-[2-(trifluoromethyl)-4-pyrimidinyl]-4-piperidinyl]-methyl-2-pyrrolidinone, or BMY-21502 as it is more commonly designated, is an improved form of drug substance having equivalent biopharmaceutical properties compared to the known anhydrous form but providing cost, safety and ecological advantages in manufacture over the known anhydrous form.

4 Claims, No Drawings

USEFUL HEMI-HYDRATE FORM OF A CEREBRAL FUNCTION ENHANCING AGENT

BACKGROUND OF THE INVENTION

This invention generally pertains to heterocyclic compounds having drug and bio-affecting properties and to their preparation and use. In particular, the invention is concerned with the hemi-hydrate form of a cognition enhancing agent, 1-[[1-[2-(trifluoromethyl)-4-pyrimidinyl]-4-piperidinyl]-methyl]-2-pyrrolidinone. This agent is more commonly known as BMY-21502, although it is also designated BMS 181168.

BMY-21502 is an orally active agent for the treatment of memory and cognitive disorders including senile dementia and Alzheimer's disease. While its mechanism of action is not completely known, beneficial effects of BMY-21502 have been demonstrated in behavorial paradigms, autoradiographic studies, cell culture studies and electrophysiologic examination of hippocampal neurons in rat brain slices.

The hemi-hydrate form of BMY-21502, the compound of this invention is likewise a cerebral function enhancer useful in treating various dementias due to degenerative processes as well as in enhancing memory and learning.

The most relevant art is believed to be the patent to Mattson, et al., U.S. Pat. No. 4,826,843 issued May 2, 1989, wherein compounds of general formula (1) were disclosed as having cognition and memory enhancing activities.

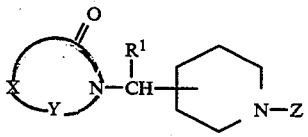

(1)

For formula (1), X is an ethylene chain or 1,2-benzo ring; Y is carbonyl or methylene; $R^1$ is hydrogen or lower alkyl; and Z is an $R^2$, $R^3$-disubstituted diazinyl ring selected from pyridazine, pyrimidine, and pyrazine ring systems. A preferred compound of the series was 1-[[1[2-(trifluoromethyl)-4-pyrimidinyl]-4-piperidinyl]-methyl]-2-pyrrolidinone (1a), hereinafter referred as BMY-21502.

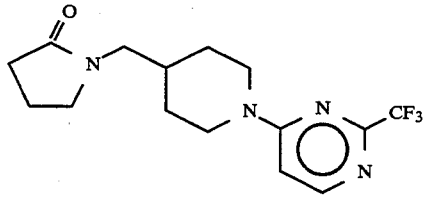

(1a)

BMY-21502 has been under clinical evaluation for the treatment of memory and cognitive disorders.

Other related art comprises oxygenated derivatives of BMY-21502 disclosed in U.S. Pat. No. 5,098,904 issued Mar. 24, 1992 to Mattson, et al. and an improved synthetic process for producing BMY-21502 which was disclosed in U.S. Pat. No. 4,963,678 issued Oct. 16, 1990 to Mattson, et al.

Although solvates such as hydrates were disclosed in general terms for formula (1) compounds by Mattson, et al. in U.S. 4,826,843, there has been no prior disclosure or appreciation of the useful novel hemi-hydrate form of BMY-21502 which constitutes the present invention. A major advantage of the hemi-hydrate form of BMY-21502 relates to increased efficiency and safety in manufacture of the hemi-hydrate compound over the anhydrous form which was specifically disclosed in the prior art.

SUMMARY AND DETAILED DESCRIPTION OF THE INVENTION

The present invention derives from the discovery of a hemi-hydrate form of BMY-21502 which is more economical, as well as more ecologically, safe to produce than the prior art anhydrous form. Although the hemi-hydrate form is less water soluble than the anhydrous product, importantly, biopharmaceutical properties are not significantly different. Compound BMY-21502 has been given orally in clinical trials directed to treatment of memory and cognitive disorders including senile dementia and Alzheimer's disease. In the course of pharmaceutical development work with this promising agent, two anhydrous polymorphs and a hemi-hydrate form of BMY-21502 were discovered.

As the need for larger amounts of the BMY 21502 drug substance increased, process development work resulted in discovering an efficient, safe and reliable crystallization process which produced exclusively the hemi-hydrate form of BMY-21502. This crystallization process provides several advantages in manufacture:

1. efficiency—the hemi-hydrate is produced in a smaller number of unit operations thereby yielding a more efficient manufacturing process;
2. safety—direct isolation from water avoids the use of manufacturing quantities of flammable organic solvent as well as eliminating worker exposure to other hazardous aspects of the use of organic solvents; and
3. environmental concern—elimination of organic solvent emissions and effluent in the crystallization process represents an important ecological advantage.

Coupled with these manufacturing advantages, the hemi-hydrate form of BMY-21502 also does not have any apparent unacceptable pharmaceutical properties.

The two anhydrous polymorphs and the hemi-hydrate compound have been examined in detail in order to establish adequate controls and specification requirements on the physical form of the drug substance used in clinical study. The anhydrous polymorphs are enantiotropic and melt at 102° and 117° with a transition temperature of about 12° C., estimated from solubility data. It is interesting that the transition temperature falls below room temperature.

BMY-21502 can be crystallized from water as a crystalline hemi-hydrate form. While controlled drying removes adventitious water, continued oven drying at 70° C. will remove the water of crystallization and provide the anhydrous forms. Thermal analysis indicates that subjecting the hemi-hydrate to 70° C. oven drying initially produces the 105°—melting anhydrous polymorph (P-105) and continued oven treatment converts the P-105 to the 117°—melting polymorph (P-117).

The hemi-hydrate contains 2.67% water by weight and melts at 95° C. with a heat of fusion of 87.9 J/g. Storage of the hemi-hydrate in controlled humidity environments results in dehydration below a critical relative humidity of 23% relative humidity and conversion into the anhydrous state. Storage under high humidity conditions rehydrates the anhydrous material yielding the hemi-hydrate form. The important parameter in this process is the critical relative humidity that is affected little by temperature. The hemi-hydrate is also light-stable.

Use of the hemi-hydrate form of BMY-21502 realizes advantages in manufacture over the anhydrous forms. The P-117 form is the preferred anhydrous form since it is the more thermodynamically stable anhydrous polymorph above the transition temperature, 12° C. Manufacture of P-117 however requires initial preparation of the hemi-hydrate form of BMY-21502 from aqueous systems then prolonged heat treatment to convert the initially obtained P-105 anhydrous form into the stable P-117 form, or recrystallization from volatile, flammable organic solvents, e.g. ethyl acetate, heptane, and the like.

The following aspects of the hemi-hydrate form comprise manufacturing advantages.

Final product can be directly isolated from water thereby avoiding the use of organic solvents with their large scale safety concerns such as fire hazard and worker exposure.

Elimination of organic solvents for product purification reduces environmentally harmful emissions/effluent as well as reducing waste management costs.

The improved process for providing the hemi-hydrate form of drug substance eliminates the need to convert the hemi-hydrate to P-117 through a prolonged oven treatment process.

The hemi-hydrate drying operation can be easily accomplished in a standard manufacturing type dryer since extended high heating (as for processing the P-117 form) is not required.

Also of importance are the biopharmaceutical properties of the hemi-hydrate form of BMY-21502. If the biopharmaceutical profile of a physical form of drug product is inferior, manufacturing advantages are to no avail.

In the instant case, solutions of the anhydrous forms and the hemi-hydrate are equivalent. Rates of dissolution and comparative solubilities are close enough in range so that there are no real practical differences between the three forms. More significantly, the two anhydrous polymorphs and the hemi-hydrate exhibit equivalent biopharmaceutical properties, including pharmacokinetic parameters and metabolite levels.

The major aspect of the present invention concerns selection of the hemi-hydrate form of BMY-21502 as an improved form of substance. With its equivalent biopharmaceutics and improved method of manufacture, the hemi-hydrate form offers a less expensive convenient form of drug substance.

Another aspect of the invention concerns use of the hemi-hydrate form of BMY-21502 as the drug substance for systemic administration to a mammal in order to enhance cerebral function or treat a disorder such as dementia, amnesia, failing memory, learning disability, mild retardation, dyslexia, aphasia, Tourette's syndrome, and the like. The administration and dosage regimen of the hemi-hydrate of BMY 21502 is considered to be the same as for an anhydrous form or in the same manner as for the reference compound of this type, piracetam, cf: Reisberg, et al. in *Drug Development Research*, 2475–80 (1982); Weng, et al., in *Rational Drug therapy*, 17(5), 1–4, 1983; and U.S. Pat. No. 5,098,904 which is hereby incorporated by reference in its entirety.

The mode of systemic administration, dosage and dosage regimen must in each case be carefully adjusted by utilization of sound professional judgment and consideration of the age, weight and condition of the recipient. Generally, the daily dose will be from about 0.1 g to about 10 g, preferably 0.5 g to 5 g, when given orally. In some instances, a sufficient therapeutic effect can be obtained at lower doses while in other, larger doses will be required. As is apparent to one skilled in clinical pharmacology, the amount of the hemi-hydrate compound comprising the daily dose may be given in a single or divided dose, taking into account those principles understood by the skilled practitioner and necessary for his practice of the art.

The term "systemic administration" as used herein refers to oral, sublingual, buccal, nasal, dermal, rectal, intramuscular, intravenous, and subcutaneous routes. Generally, it will be found that when the compound of the present invention is administered orally which is the preferred route, a slightly larger quantity of the active drug may be required to produce the same effect as a somewhat smaller quantity when given parenterally. In accordance with good clinical practice, it is preferred to administer the instant compound at a concentration level which will produce effective beneficial effects without causing any harmful or untoward side effects.

Therapeutically, the instant compound is generally given as a pharmaceutical composition comprised of an effective cerebral function enhancing amount of the hemi-hydrate and a pharmaceutically acceptable carrier. Pharmaceutical compositions for effecting such treatment will contain a major or minor amount (e.g. from 95% to 0.5%) of the compound of the present invention in combination with a pharmaceutical carrier, the carrier comprising one or more solid, semi-solid, or liquid diluent, filler and formulation adjutant which is non-toxic, inert and pharmaceutically acceptable. Such pharmaceutical compositions are preferably in dosage unit forms; i.e. physically discrete units having a predetermined amount of the drug corresponding to a fraction or multiple of the dose which is calculated to produce the desired therapeutic response. In usual practice, the dosage units contain 1, ½, ⅓, or less of a single dose. A single dose preferably contains an amount sufficient to produce the desired therapeutic effect upon administration at one application of one or more dosage units according to the predetermined dosage regimen, usually a whole, half, third, or less of the daily dosage administered once, twice, three or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral compositions are in the form of tablets, capsules, and may contain conventional excipients such as binding agents (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica) disintegrants (e.g. starch) and wetting agents (e.g. sodium lauryl sulfate). Solutions or suspensions of the hemi-hydrate compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of the active compound in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

DESCRIPTION OF SPECIFIC EMBODIMENTS

EXAMPLE 1

Manufacture of the Hemi-Hydrate Form of BMY-21502

The process description sets forth the currently preferred large scale method for preparation of the hemihydrate form of BMY-21502. The chemistry and preparation of the reactants was disclosed in U.S. Pat. No. 4,826,843 which is hereby incorporated by reference.

A. 1-[(4-Piperidinyl)methyl]-2-pyrrolidinone Hydrochloride Hydrate.

A solution of 1-(4-pyridinylmethyl)-2-pyrrolidinone hydrochloride (15.05 g, 0.0707 mole; prepared from 2-pyrrolidinone and 4-pyridinylmethyl chloride), HCl (10 mL of an 8N solution in absolute ethanol) and absolute ethanol (100 mL) was hydrogenated at 60 psi with $PtO_2$ (1.0 g) for 72 hours. The mixture was filtered and the filtrate reduced in vacuo to give a white solid. The crude product was recrystallized from isopropanol to give 13.03 g (83%) of product as a white powder, m.p. 212°–214°.

B. The hemi-hydrate product is prepared by the reaction of 4-chloro-2-(trifluoromethyl) pyrimidine with 1-[(4-piperidinyl)methyl]-2-pyrrolidinone HCl in an alkaline aqueous system.

REACTION SCHEME

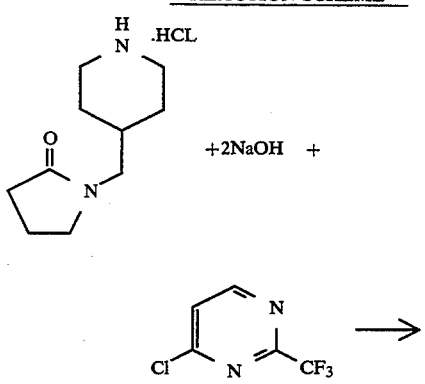

+2NaOH +

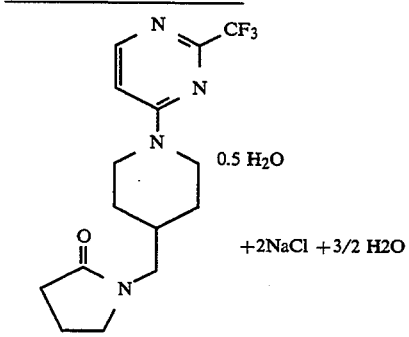

-continued
REACTION SCHEME

+2NaCl +3/2 H2O

A slight molar excess of the chloropyrimidine intermediate (neat) is added slowly to an aqueous solution of the piperidinylmethyl-2-pyrrolidinone intermediate at pH 8.3–8.7. while 10 wt % NaOH is added simultaneously to maintain pH 8.3–8.7. The temperature is maintained at 50°–55° C. throughout. Seed crystals of the desired product are present from the beginning.

The reaction to produce the hemi-hydrate of BMY 21502-3 is rapid, and the product crystallizes as it forms. The addition rates and stirring rate are adjusted so that the product crystallizes in the desired rod-like crystal habit. Early in the reaction when the product first begins to crystallize, the reactant flows are interrupted, additional seed is added, and the developing crystals are allowed to mature with continued stirring. Once crystallization in the proper habit is verified, the additions are resumed. When the addition of the pyrimidine intermediate is complete, base addition is continued until the mixture stabilizes at pH 8.5–8.7.

After cooling the reaction mixture, the product is filtered and washed with water, giving an off-white to white solid. This solid is dried at 22°–28° C. and reduced pressure to a moisture content of 2.4–2.9 wt % based on Karl Fisher (KF), or similar coulometric titration (theory 2.67%). The product is stored in a sealed container. The yield of product as the hemihydrate is about 90M %.

I claim:

1. The hemi-hydrate form of 1-[[1-[2-(trifluoromethyl)-4-pyrimidinyl-4-piperidinyl]methyl-]-2-pyrrolidinone.

2. The method for enhancing cerebral function in a mammal in need of such treatment which comprises systemic administration to the mammal of an effective dose of the hemi-hydrate compound of claim 1.

3. The method for treating a disorder in a mammal in need of such treatment, the disorder selected from the group consisting of dementia, amnesia, failing memory, learning disability, mild retardation, dyslexia, aphasia and Tourette's syndrome; the treatment comprising systemic administration to the mammal of an effective dose of the hemi-hydrate compound of claim 1.

4. A pharmaceutical composition for the enhancement of cerebral function comprising a pharmaceutical carrier and the hemi-hydrate compound of claim 1.

* * * * *